United States Patent [19]

Willard et al.

[11] Patent Number: 4,701,711
[45] Date of Patent: Oct. 20, 1987

[54] NUCLEAR MAGNETIC RESONANCE APPARATUS WITH SWITCHED ATTENUATOR

[75] Inventors: Reginald A. Willard, Middlesex; William S. Percival, London, both of England

[73] Assignee: National Research Development Corporation, London, England

[21] Appl. No.: 857,310

[22] Filed: Apr. 30, 1986

[30] Foreign Application Priority Data

May 3, 1985 [GB] United Kingdom ............. 8511354
May 3, 1985 [GB] United Kingdom ............. 8511382

[51] Int. Cl.⁴ ............................................. G01R 33/20
[52] U.S. Cl. ............................. 324/322; 324/303; 307/262; 307/555; 328/223
[58] Field of Search ............ 324/303, 306, 309, 314, 324/318, 322; 307/262, 264, 362, 540, 555, 556; 328/113, 223

[56] References Cited

U.S. PATENT DOCUMENTS

| 2,527,474 | 10/1950 | Alvarez | 328/223 |
| 3,360,732 | 12/1967 | Haugh et al. | 328/223 |
| 3,617,867 | 11/1971 | Herzog | 324/303 |
| 3,763,478 | 10/1973 | Yoshizawa et al. | 328/113 |
| 4,350,955 | 9/1982 | Jackson et al. | 324/303 |
| 4,565,968 | 1/1986 | Macovski | 324/306 |
| 4,629,986 | 12/1986 | Clow et al. | 324/303 |

FOREIGN PATENT DOCUMENTS 2141236 12/1984 United Kingdom .

Primary Examiner—Stewart J. Levy
Assistant Examiner—Kevin D. O'Shea
Attorney, Agent, or Firm—Cushman, Darby & Cushman

[57] ABSTRACT

Nuclear magnetic resonance is excited in surrounding fluids by pulsing a first winding which with a capacitor forms a resonant circuit. In order to observe signals induced by NMR in the first winding between pulses, the pulses are attenuated by connecting resistors across a second winding inductively coupled to the first winding. Connection of the resistors is made when required by forward biasing two MOSFETs connected "back to back" to reduce transients when the MOSFETs cease conduction. A switching pulse for the MOSFETs which has a steep rising edge and an exponential trailing edge has been found advantageous.

10 Claims, 7 Drawing Figures

NUCLEAR MAGNETIC RESONANCE APPARATUS WITH SWITCHED ATTENUATOR

The present invention relates to a resonant circuit in combination with a switched attenuator which is brought into operation where rapid attenuation of oscillations in the resonant circuit is required. The invention is particularly but not exclusively of use with nuclear magnetic resonance (NMR) apparatus.

As is described in British Patent Application No. 2141236A one form of nuclear magnetic logging requires the application of current pulses to a solenoid in order to generate a radiofrequency magnetic field. The same solenoid may also serve to pick up nuclear magnetic resonance signals but in order to do so the disturbing oscillations in the solenoid must be rapidly attenuated. In fact attenuation by a factor of more than $10^9$ in a period of about 500 microseconds is typically required and this presents a considerable problem in view of the transients caused by such rapid attenuation.

Apparatus similar to that of the above mentioned patent application may also be employed in other types of cavity or orifice, for example a miniature version may be employed for NMR in the human or animal body.

In this specification the term switching device means a device having a control electrode and two other electrodes, the application of a suitable control signal to the control electrode changing the device from a non-conducting state in which the impedance between the said other electrodes is substantially open circuit to a conducting state in which the said impedance has a low value.

According to one aspect of the present invention there is provided nuclear magnetic resonance apparatus comprising first and second means for generating opposed magnetic fields in a space containing a solenoidal first winding having its axis aligned with the fields, and containing a core of magnetic material, reactive impedance connected across the first winding to form a resonant circuit, means for applying bursts of oscillations to the resonant circuit, means for deriving signals representative of signals induced in the first winding between bursts, a centre tapped second winding inductively coupled to the first winding, first and second switching devices as hereinbefore specified arranged when in the conducting state to connect resistance means across the second winding, with the connection such that transient voltages occurring when the devices enter their non-conducting states are in opposition in the two halves of the second winding, bias means for biassing the devices into the non-conducting state, and pulse generating means for applying switching pulses to control electrodes causing the devices to enter the conducting state when oscillations in the resonant circuit are to be attenuated, the combined resistance of the resistance means and the devices when conducting, when referred to the first winding being substantially equal to half the reactance of an inductor comprising the first and second windings and the core when also referred to the first winding.

According to another aspect of the present invention there is provided a resonant circuit for use where rapid attenuation of oscillations in the circuit is required on demand, comprising an inductor having a first winding, a second winding in two halves defined by a centre tap, reactive impedance connected across the first winding to form a resonant circuit, first and second switching devices as hereinbefore specified arranged when in the conducting state to connect resistance means across the second winding, with the connection such that transient voltages occurring when the devices enter their non-conducting states are in opposition in the two halves of the second winding, bias means for biassing the devices into the non-conducting state, and pulse generating means for applying switching pulses to control electrodes causing the devices to enter the conducting state when oscillations in the resonant circuit are to be attenuated, the combined resistance of the resistance means and the devices when conducting, when referred to the first winding being substantially equal to half the reactance of the inductor when also referred to the first winding.

The switching devices may be metal oxide silicon field effect depletion transistors (MOSFETs) which in the conducting state have an impedance of one or two Ohms or less between source and drain terminals.

The resistance means preferably comprises first and second resistors corresponding to the first and second devices, with each first and second resistor connected between a respective end of the second winding and one of the said other electrodes of the corresponding device.

The bias means may include means for equalizing the bias signals at the control electrodes when the devices are in the non-conducting state.

When the devices are MOSFETs, the source or drain electrodes may be connected together and to the centre tap by way of a resistor. The centre tap and one electrode of a capacitor forming the reactive impedance may be connected to a common terminal such as an earth for the circuit.

The major part of the attenuation mentioned above can be achieved by connecting the resistance means across the inductor, and further attenuation, if required, can be obtained by using a particular waveform (as described below) to excite the first winding. The technique of fast attenuation by connecting a resistor across the complete inductor of a resonant circuit where the resistor has a value equal to half the reactance of the inductor is known, but the problem of resulting transients remained.

In general any switching process produces transients and if the switching is sufficiently rapid the transients may contain spurious components within a bandwidth of interest. In the case of nuclear magnetic logging a typical bandwidth of interest is from 2 to 5 kHz centred on 41.5 kHz. With the circuit of the invention, since the transients are in opposition in the two halves of the second winding, transients in the first winding are very significantly reduced.

The biassing means preferably also includes means for applying an adjustable bias voltage to the control electrodes in order to minimise transients within a band of interest.

According to a further feature of the invention the pulse generating means includes means for shaping the switching pulses applied to the gate electrodes to give the pulses a relatively abrupt leading edge and an exponential trailing edge.

An embodiment of the invention will now be described by way of example, with reference to the accompanying drawings in which.

Figure 1:
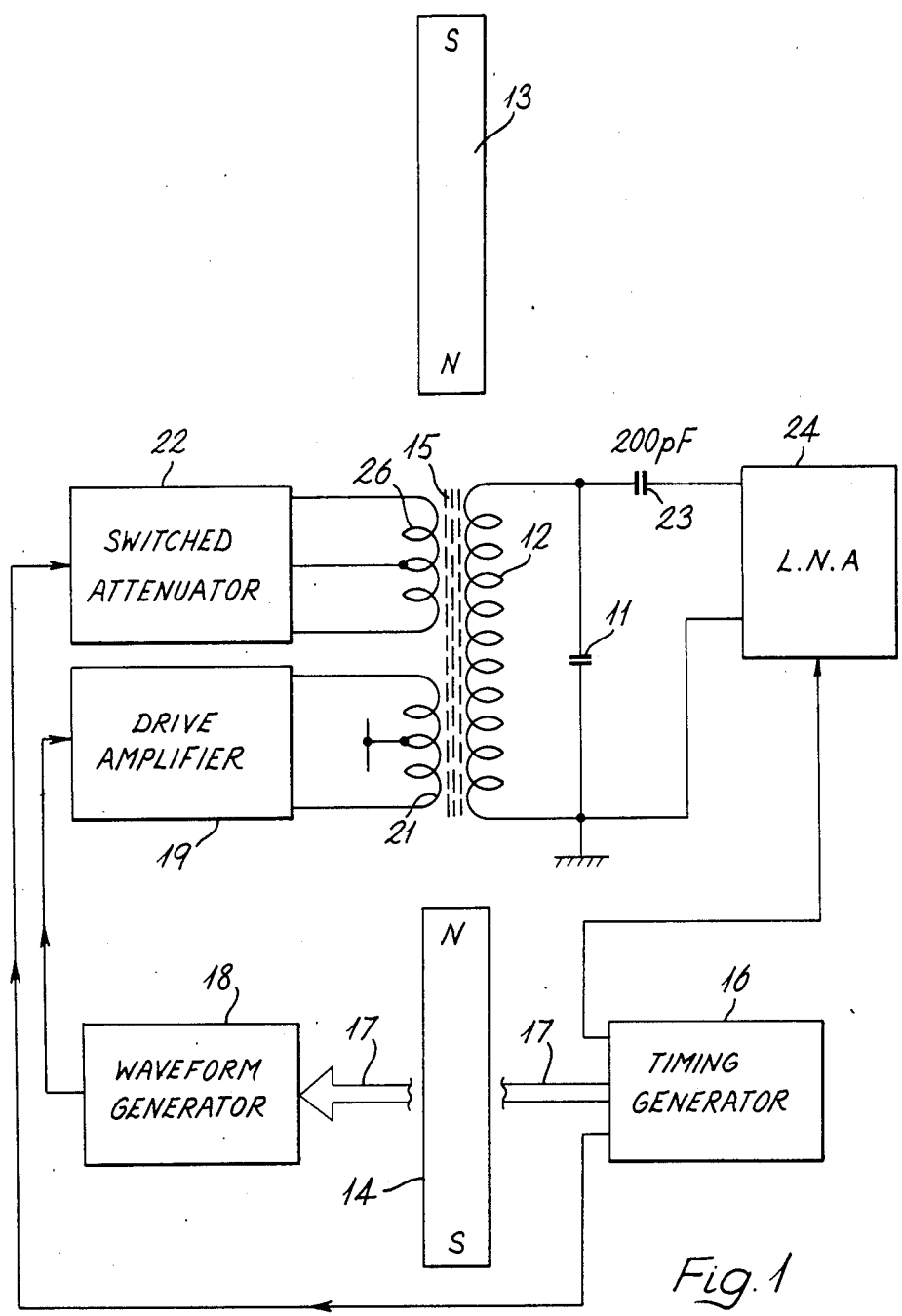
FIG. 1 is a block diagram of NMR apparatus employing the invention.
Figure 2:
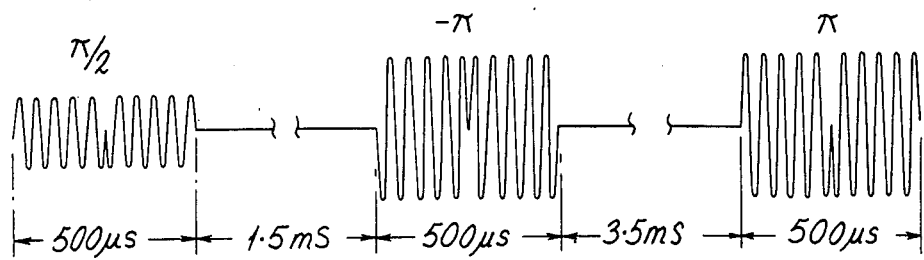
FIG. 2 shows pulses generated by the waveform generator of FIG. 1.
Figure 3:
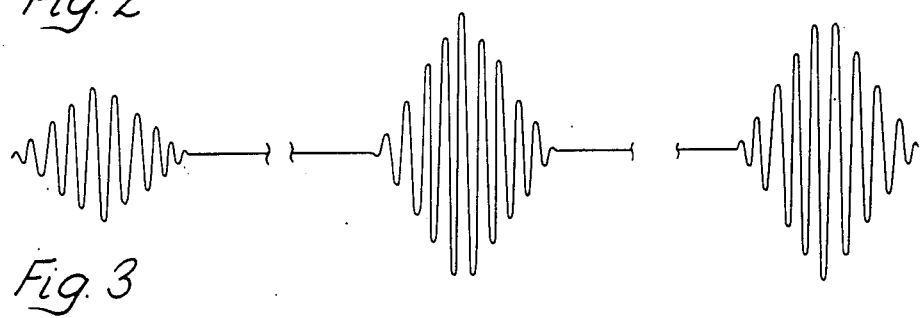
Figure 4:
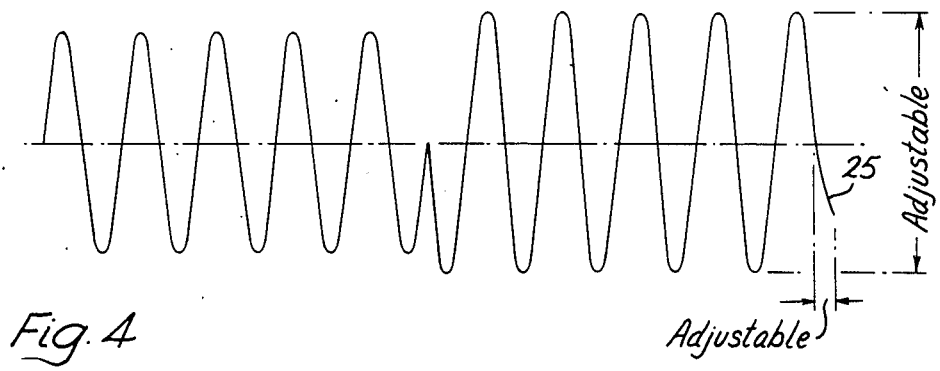
Figure 5:
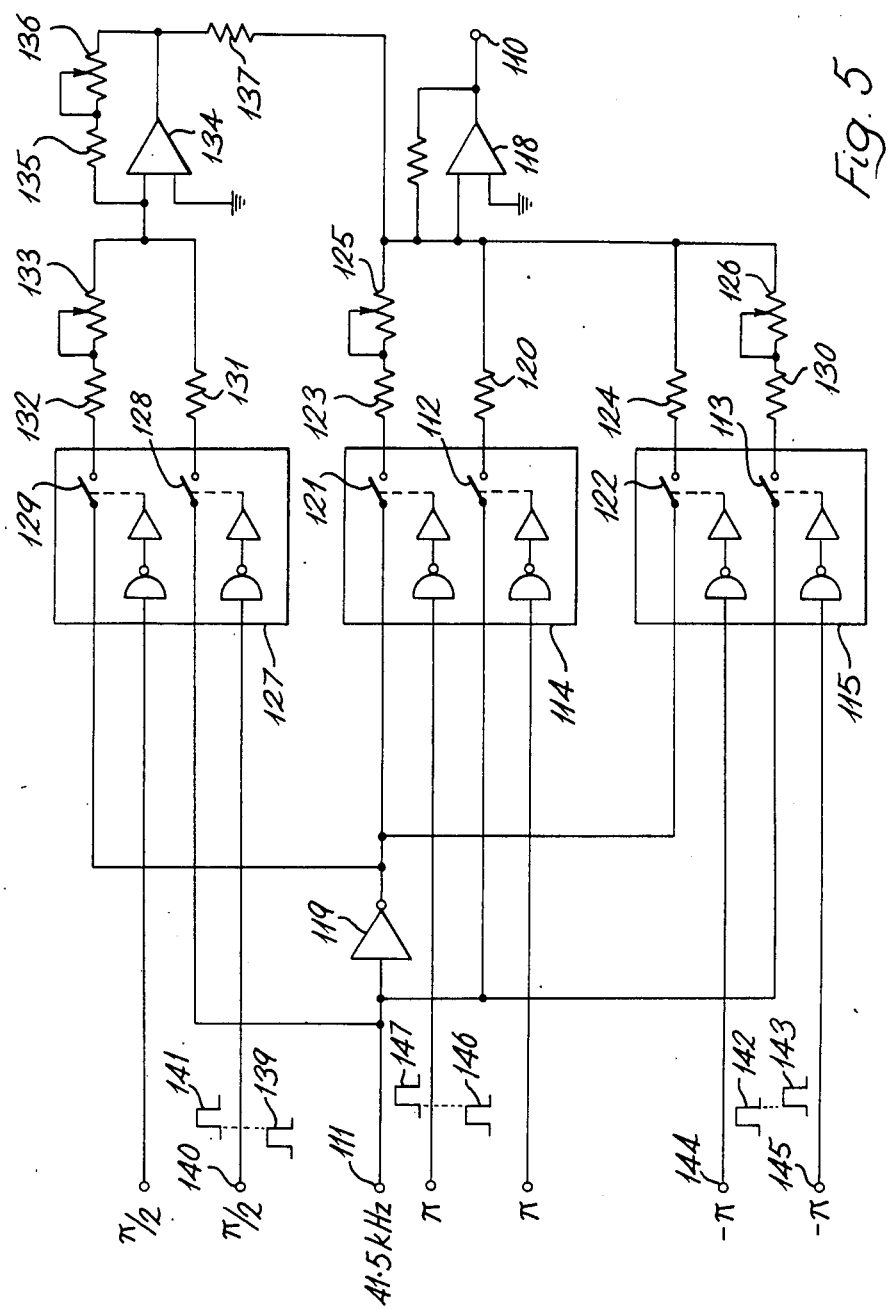
Figure 6:
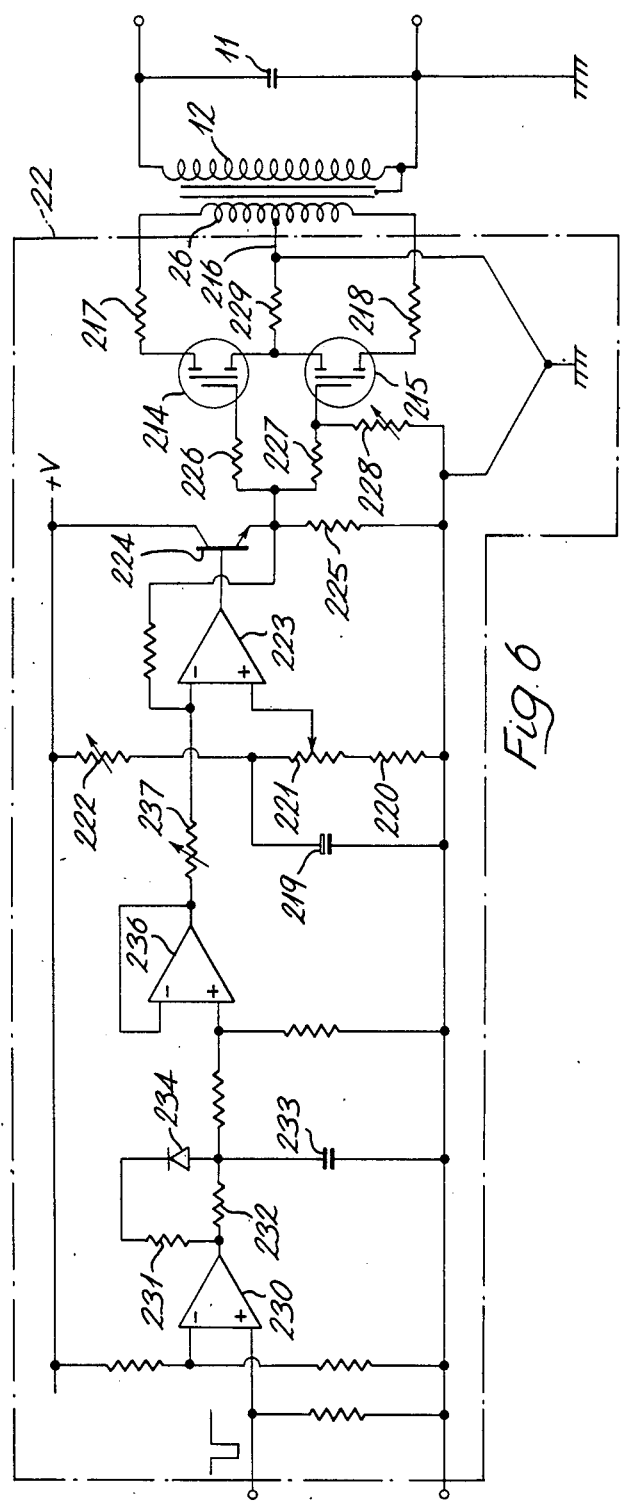
Figure 7:
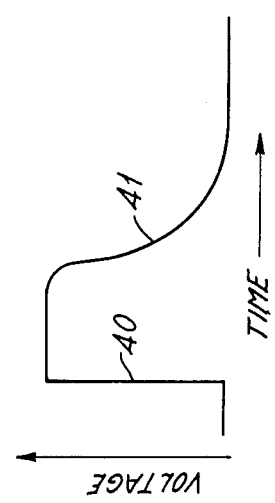

FIG. 3 shows pulses in a high Q resonant circuit resulting from the pulses of FIG. 2, FIG. 4 shows one of the pulses of FIG. 2 in more detail, FIG. 5 is a block diagram of the waveform generator of FIG. 1, FIG. 6 is a diagram of a circuit according to the invention in a form suitable for use as the switched attenuator of FIG. 1, and FIG. 7 shows the waveform of a switching pulse employed in the circuit of FIG. 6.

An NMR system employing the invention is first described. In FIG. 1 a capacitor 11, a winding 12 in the form of a solenoid, two permanent magnets 13 and 14, and a core 15 (for the winding 12) of high permeability ferrimagnetic material are arranged to function in the way described in the above mentioned British Patent Application No. 2141346A. However as mentioned above the apparatus, perhaps modified in size, may be employed for other NMR applications. The magnets, the winding 12 and its core and much, or all, of the electronics shown in FIG. 1 are positioned in a cylindrical housing (not shown) which, in use, is for example lowered down a borehole, or inserted into a body cavity.

A timing generator 16 provides a sequence of pulses along a bus 17 to cause a waveform generator 18 to generate a series of pulses of the form shown in FIG. 2 as input signals for a balanced drive amplifier 19 feeding a winding 21 wound over the winding 12. The winding 21 induces waveform pulses in the winding 12 which excite NMR in a fluid (such as water or oil) in a geological formation surrounding a borehole, or in body tissue surrounding a cavity. The waveform generator is described in more detail below. The waveform induced in the resonant circuit formed by the winding 12 and the capacitor 11 is as shown in FIG. 3 and at the end of each burst of oscillations forming a pulse, any residual voltage is attentuated by a switched attenuator 22 coupled to a winding 26 wound over the winding 12. The attenuator 22 is described in more detail below. In the intervals between the bursts of oscillations when the exciting voltage has decayed and been attenuated sufficiently NMR signals are picked up by the winding 12 and passed by way of a capacitor 23 to a low noise amplifier 24. Limiting diodes (not shown) are connected at the input to the amplifier to reduce the drive voltage during the bursts of oscillations of FIG. 3. One or more F.E.T. shorting switches (not shown) may also be included in the amplifier and operated by the timing generator 16 to be closed while the drive voltage is present.

The pulses (formed by bursts of oscillations) in FIG. 3 have the general form of the Carr-Purcell sequence which is known for use in nuclear magnetic resonance (NMR). However, the pulses shown differ from the normal Carr-Purcell sequence in that there is a 180° phase change at the centre of each pulse. As is usual the sequence starts with a half amplitude pulse designated $\pi/2$ and is then followed by full amplitude pulses of alternating phase starting with a pulse of opposite phase to the $\pi/2$ pulse. In view of the change of phase at the beginning of each pulse the following pulses are knows as $-\pi$ and $\pi$ pulses, alternately. $\pi$ and $-\pi$ pulses are, in this example, separated by intervals of approximately 4 milliseconds (from start to start) while the initial interval between the $\pi/2$ pulse and the first $-\pi$ pulse is approximately 2 milliseconds (from start to start). Each $\pi/2$ pulse, $-\pi$ and $\pi$ pulse has a duration of approximately 500 microseconds.

When the first half of one of the pulses of FIG. 2 is applied to a high Q resonant circuit such as that used in an NMR borehole logging device of the type mentioned above where the resonant circuit includes a solenoid positioned between two permanent magnets, the result is a linear growth in amplitude of oscillations in the solenoid, provided the frequency of the sinusoidal waveform is equal to or near the resonant frequency of the resonant circuit. The linear growth in amplitude is followed by a linear decay starting when the phase change of 180° occurs. Such pulses in a resonant circuit are shown in FIG. 3.

At the peak of the envelope of FIG. 3 in a $\pi$ or $-\pi$ pulse the amplitude of the voltage waveform is of the order of 250 volts and it is required that the envelope decays linearly to zero volts. This is achieved by making each $\pi$ or $-\pi$ pulse in the form shown in FIG. 4 where the first portion is of constant duration and constant amplitude but the second portion is of adjustable amplitude and duration. In setting up the apparatus the waveform across the resonant circuit is observed, for example using an oscilloscope, and the second half of each pulse is adjusted to give the required linear decay to zero. Thus a portion 25 can be advanced (as shown) or retarded beyond the position where the signal would finish at a cross-over point so that the second half of each pulse can be made, with the assistance of the amplitude adjustment, to "cancel" each first half as exactly as possible so that the sinusoidal waveform in each pulse finishes as near to zero as possible. The first half of each pulse of FIG. 4 consists of 5 to 10 sinusoidal oscillations, as does the second half.

The waveform of FIG. 4 in the pulse sequence of FIG. 2 appears at an output terminal 110 of FIG. 5 and is formed by switching a sinusoidal waveform applied at an input terminal 111 without inversion and by way of an inverting amplifier 119, alternately. For NMR, the waveform applied at the terminal 111 is at the Larmor frequency which depends on the magnetic field generated and the material subjected to the field. As an example the Larmor frequency is taken to be 41.5 kHz. In order to generate the first half of $\pi$ bursts and the second half of $-\pi$ bursts, the input terminal 111 is connected by way of contacts 112 and 113 in dual analogue switches 114 and 115 and resistors 120 and 130, respectively, to the input of a summing amplifier 118. A variable resistor 126 is connected between the resistor 130 and the amplifier 118. The second half of each $\pi$ burst and the first half of each $-\pi$ burst is obtained by connecting the output of an inverting amplifier 119, connected to the input terminal 111 by way of contacts 121 and 122 and resistors 123 and 124 to the summing amplifier 118. A variable resistor 125 is connected between the resistor 123 and the summing amplifier 118.

Similar connections are provided to generate the $\pi/2$ bursts, using a dual analogue switch 127 with contacts 128 and 129, resistors 131 and 132 and a variable resistor 133. However a variable gain amplifier 134 with fixed and variable resistors 135 and 136 and an output resistor 137 are inserted at the input to the summing amplifier 118.

In operation, a gating pulse 139 is first applied to a terminal 140 generating the first half of the $\pi/2$ pulse by closing the contacts 128 and gating the 41.5 kHz signal to the amplifier 118 and so to the output terminal 110.

The second half is obtained by starting a gating pulse 141 concurrently with the end of the pulse 139 to gate a similar but inverted pulse of the 41.5 kHz signal to the amplifier 118 by way of the contacts 129. Thus the required phase change is obtained in the middle of the $\pi/2$ pulses. The variable resistor 136 is used to adjust the amplitude of the $\pi/2$ pulses and the variable resistor 133 is used to adjust the amplitude of the second half of such pulses. Each pulse 139 and 141 has a duration of approximately 250 microseconds.

After an interval of approximately 1.5 milliseconds a gating pulse 142 is applied to a terminal 144, followed immediately by a gating pulse 143 applied to a terminal 145. Inverted and non-inverted cycles of the 41.5 kHz signal reach the output terminal 110 by way of the contacts 122 and 113, respectively, to give $-\pi$ pulses. The variable resistor 126 allows the amplitude of the non-inverted cycles to be adjusted as indicated in FIG. 3. Each pulse 142 and 143 also has a duration of approximately 250 microseconds as do later pulses 146 and 147.

After an interval of approximately 3.5 milliseconds gating pulses 146 and 147 occur switching contacts 112 and 121 successively and generating the $\pi$ pulses, with the amplitude of the inverted portion adjustable by means of the variable resistor 125.

Pulse pairs 142, 143 and 146, 147 are now generated alternately at about 4 millisecond intervals until the end of the exciting pulse sequence is reached. The $\pi/2$, $-\pi$, $\pi$ sequence is then repeated after a predetermined interval.

The gating pulses 139, 142 and 146 are derived in the timing generator 16 by division from a crystal controlled master oscillator (not shown) and pulses from this oscillator also trigger respective monostable circuits (not shown) which provide the pulses 140, 143 and 147. The monostable circuits are adjustable to give the adjustment 25 of the duration of the second halves of the $\pi$, $-\pi$, and $\pi/2$ pulses. The gating pulses reach the waveform generator 18 by way of the bus 17.

The terminal 110 at the output of the circuit of FIG. 5 is connected by way of the drive amplifier 19 to the winding 21 which has a low Q. The winding 12 has a high Q secondary winding and with the capacitor 11 forms the resonant circuit (in this example resonant at 41.5 kHz) in which the waveform of FIG. 3 appears.

The switched attenuator 22 shown in FIG. 6 is now described. When the oscillations of FIG. 3 in the resonant circuit (the capacitor 11 and the winding 12) decay they are further rapidly attenuated by the switched attenuator 22 connected to the winding 26. The attenuator 22 comprises two MOSFETs 214 and 215 of the depletion type (n or p channel) each with source electrode connected to a centre tap 216 of the winding 26 by way of a resistor 229 typically of value 10 kOhms. Resistors 217 and 218 are connected between opposite ends of the winding 26 and drain terminals of the FEs (often each about 1 Ohm) and referred to the winding 12 equals half the reactance of the inductor formed by the windings 12, 21 and 26 and the core 15 when also referred to the winding 12. As is known, the connection of a resistance of this value across the inductor of a resonant circuit causes attenuation of oscillations in the circuit to occur at the maximum possible rate. In many applications the MOSFETs 214 and 215 may be International Rectifier type IRF 830 or similar, which while conducting have a resistance of about 1 Ohm and the resistors 217 and 218 may then be 1.5 Ohms each assuming that the reactance of the above mentioned inductor referred to the winding 26 is 5 Ohms.

In the absence of a drive signal, the FETs 214 and 215 are biassed to their non-conducting state by a bias voltage derived from a resistor 220 and variable resistors 221 and 222 connected across a positive supply voltage. A capacitor 219 decouples the resistors 220 and 221. The voltage from these resistors is applied by way of an operational amplifier 223, a bipolar transistor 224 with emitter resistor 225 and two equal resistors 226 and 227, typically of value 100 Ohms, in series with the gate electrodes of the respective FETs. Fine and coarse adjustment of the bias voltage is achieved by adjustment of the resistors 221 and 222, respectively, and a variable resistor 228, typically of value 10 kOhms, is connected between the gate of the FET 215 and earth to balance the gate electrodes to earth over the region of the FET characteristics where transition between low and high resistance takes place.

When it is required to attenuate oscillations in the resonant circuit a positive pulse from the timing generator 16 is applied to the transistor 224 switching on both the FETs. The FETs then conduct together passing a rapidly decaying alternating current driven by the voltage across the winding 26. When the FETs are switched to the non-conducting state at the end of the pulse, any transient voltages which appear across the FETs 214 and 215 are in opposition at the primary winding 26 and therefore cancel. Careful adjustment of the gate electrode bias and balance to earth is required to ensure that negligible spurious signals are produced in the resonant circuit within a given bandwidth which may, for example, be as mentioned above.

The switching pulse required by the FETs is several volts and must be reduced to considerably less than a microvolt to prevent leakage into the resonant circuit. If a square pulse were used considerable voltage components would occur for example in the bandwidth mentioned above and these components could not be entirely removed by balancing. For this reason the switching pulse is shaped as shown in FIG. 7 with an abrupt leading edge 40 and an approximately exponential trailing edge 41 preferably having a substantially constant rate of change which does not give rise to significant components within a required bandwidth. In the examples shown a negative going rectangular pulse of duration about 500 microseconds is applied to the non-inverting input of an operational amplifier 230 with output connected to a pulse shaping circuit comprising a 500 Ohm resistor 231, a 10 kOhm resistor 232, a 6800 pF capacitor 233 and a diode 234. The rise time of the resultant pulse is determined by the resistor 231 and the diode 234 and the exponential decay by the resistor 232 and the capacitor 233. The values of these components are chosen empirically but they are not critical. The output from the pulse shaping circuit is passed by way of an operational amplifier 236 connected as a buffer and a variable resistor 237 which enables the amplitude of the pulses to be adjusted as required.

Capacitive coupling between the windings 21 and 26 and the winding 12 of the inductor causes an additive component from switching transients and must therefore be eliminated as far as possible. In this example windings 21 and 26 are each wound with a thin coaxial cable, the outer of which is earthed at one point. Further these windings are wound over the whole length of the winding 12 to reduce magnetic field leakage.

The switched attenuator of the invention can be used to attenuate oscillations in many resonant circuits having a wide variety of applications in addition to the resonant circuit of the above described NMR apparatus.

We claim:

1. A resonant circuit for use where rapid attenuation of oscillations in the circuit is required on demand, comprising an inductor having a first winding, a second winding in two halves defined by a centre tap, reactive impedance connected across the first winding to form a resonant circuit, first and second switching devices, each said device having a control electrode and two other electrodes, an application of a suitable control signal to the control electrode changing the device from a non-conducting state in which the impedance between the said other electrodes is substantially open circuit to a conducting state in which the said impedance has a low value, the said devices being arranged when in the conducting state to connect resistance means across the second winding, with the connection such that transient voltages occurring when the devices enter their non-conducting states are in opposition in the two halves of the second winding, bias means for biasing the devices into the non-conducting state, and pulse generating means for applying switching pulses to control electrodes causing the devices to enter the conducting state when oscillations in the resonant circuit are to be attenuated, the combined resistance of the resistance means and the devices when conducting, when referred to the first winding being substantially equal to half the reactance of the inductor when also referred to the first winding.

2. A circuit according to claim 1 wherein the first and second switching devices are metal oxide silicon field effect depletion transistors (MOSFETs) which in the conducting state have an impedance of one or two Ohms or less between source and drain terminals.

3. A circuit according to claim 2 wherein the source or drain electrode of one of the MOSFETs is connected to the corresponding electrode of the other MOSFET and to the centre tap of the second winding by way of a resistor, and the centre tap and one electrode of a capacitor forming the reactive impedance are connected to a common terminal.

4. A circuit according to claim 1 wherein the resistance means comprises first and second resistors corresponding to the first and second devices, with each first and second resistor connected between a respective end of the second winding and one of the said other electrodes of the corresponding device.

5. A circuit according to claim 1 wherein the bias means include means for equalising the bias signals at the control electrode when the devices are in the non-conducting state.

6. A circuit according to claim 1 wherein the biassing means include means for applying an adjustable bias voltage to the control electrodes in order to minimise transients within a band of interest.

7. Nuclear magnetic resonance apparatus comprising first and second means for generating opposed magnetic fields in a space containing a solenoidal first winding having its axis aligned with the fields and containing a core of magnetic material, reactive impedance connected across the first winding to form a resonant circuit, means for applying bursts of oscillations to the resonant circuit, means for deriving signals representative of signals induced in the first winding between bursts, a centre tapped second winding inductively coupled to the first winding, first and second switching devices, each said device having a control electrode and two other electrodes, the application of a suitable control signal to the control electrode changing the device from a non-conducting state in which an impedance between the said other electrodes is substantially open circuit to a conducting state in which the said impedance has a low value, the said devices being arranged when in the conducting state to connect resistance means across the second winding, with the connection such that transient voltages occurring when the devices enter their non-conducting states are in opposition in the two halves of the second winding, bias means for biassing the devices into the non-conducting state, and pulse generating means for applying switching pulses to control electrodes causing the devices to enter the conducting state when oscillations in the resonant circuit are to be attenuated, the combined resistance of the resistance means and the devices when conducting, when referred to the first winding being substantially equal to half the reactance of an inductor comprising the first and second windings and the core when also referred to the first winding.

8. A resonant circuit according to claim 7 wherein the first and second means for generating magnetic fields comprise respective permanent magnets.

9. Apparatus according to claim 7 wherein the first and second switching devices are metal oxide silicon field effect depletion transistors (MOSFETs) which in the conducting state have an impedance of one or two Ohms or less between source and drain terminals and the source or drain electrode of one of the MOSFETs is connected to the corresponding electrode of the other MOSFET and to the centre tap of the second winding by way of a resistor, and the centre tap and one electrode of a capacitor forming the reactive impedance are connected to a common terminal.

10. Apparatus according to claim 7 wherein the resistance means comprises first and second resistors corresponding to the first and second devices, with each first and second resistor connected between a respective end of the second winding and one of the said other electrodes of the corresponding device.

* * * * *